United States Patent [19]

Marx et al.

[11] Patent Number: 4,567,277
[45] Date of Patent: Jan. 28, 1986

[54] SALTS OF 2-(METHOXY-CARBONYLAMINO)-BENZIMIDAZOLE

[75] Inventors: Hans-Norbert Marx, Buehl-Weitenung; Ernst-Heinrich Pommer, Limburgerhof, both of Fed. Rep. of Germany

[73] Assignee: BASF Aktiengesellschaft, Fed. Rep. of Germany

[21] Appl. No.: 734,823

[22] Filed: May 16, 1985

Related U.S. Application Data

[63] Continuation of Ser. No. 421,417, Sep. 22, 1982, abandoned.

[30] Foreign Application Priority Data

Sep. 28, 1981 [DE] Fed. Rep. of Germany ....... 3138575

[51] Int. Cl.$^4$ .......................................... C07D 235/32
[52] U.S. Cl. .................................... 548/306; 514/388
[58] Field of Search ......................................... 548/306

[56] References Cited

U.S. PATENT DOCUMENTS

| 3,657,443 | 4/1972 | Klopping | 548/306 |
| 3,852,460 | 12/1974 | Littler et al. | 548/304 |
| 3,929,823 | 12/1975 | Beard et al. | 548/306 |
| 4,287,199 | 9/1981 | Wollweber et al. | 548/306 |

FOREIGN PATENT DOCUMENTS

| 2417008 | 11/1975 | Fed. Rep. of Germany . |
| 2180991 | 11/1973 | France . |
| 7501295 | 8/1975 | Netherlands . |

*Primary Examiner*—Robert W. Ramsuer
*Attorney, Agent, or Firm*—Keil & Weinkauf

[57] ABSTRACT

Fungicides containing an aqueous solution of a salt of 2-(methoxy-carbonylamino)-benzimidazole and a weak acid, and methods of controlling fungi and preserving wood using these solutions.

2 Claims, No Drawings

SALTS OF 2-(METHOXY-CARBONYLAMINO)-BENZIMIDAZOLE

This application is a continuation of application Ser. No. 421,417, filed on Sept. 22, 1982 now abandoned.

The present invention relates to fungicides containing a salt of 2-(methoxy-carbonylamino)-benzimidazole and a weak acid, eg. a sulfonic acid, and a method of protecting plants from fungal attack and for preserving wood.

2-(Methoxy-carbonylamino)-benzimidazole (BCM) is known to have a fungicidal action (R. Wegler, Chemie der Pflanzenschutz- und Schädlingsbekämpfungsmittel, Volume 4, pages 180 et seq., Springer-Verlag, Berlin, 1977, and German Published Application DAS No. 2,040,069). It is also known that salts of this active ingredient and an acid having an ionization constant of greater than $1 \times 10^{-5}$ can be used in the form of an aqueous solution having a pH of 4 or less for controlling fungal diseases of plants (German Laid-Open Application DOS No. 1,792,688).

We have found that aqueous solutions of salts of 2-(methoxy-carbonylamino)-benzimidazole, prepared using weak acids, can be used for protecting wood from destruction by fungi or bacteria and are particularly active against phytopathogenic fungi and, surprisingly, are well tolerated by plants.

For the purposes of the invention, weak acids are weak inorganic or organic acids, eg. fluoboric acid (HBF$_4$), hexafluorosilicic acid, monoesters or diesters of phosphoric acid and alcohols (such as butanol or polyethylene glycol) or sulfonic acids, such as sulfamic acid or aliphatic or aromatic sulfonic acids, in particular aromatic sulfonic acids, eg. phenylsulfonic acids, which can contain other groups, eg. the hydroxyl, amino or carboxyl group, in the organic radical, eg. the phenyl radical, such as 4-phenolsulfonic acid. Aromatic sulfonic acids which contain more than one sulfonic acid group in the molecule can also be used, eg. the corresponding di- or tri-sulfonic acids. If biologically active acids are used, the protective effect of the solution may be increased, for example fluoboric acid additionally contains fungicidally active fluorine and boron. The 4-phenolsulfonic acid salt of BCM is preferred.

The aqueous solutions of the salts contain from 0.01 to 5% by weight, in particular from 0.025 to 1% by weight, of BCM, calculated as BCM without the acid. The pH of the solutions can vary within a wide range, and is preferably from 1.5 to 4.5. The molar ratio of BCM to acid is, for example, from 1:1 to 1:2.5, and is preferably 1:2. A larger excess of acid does no harm, provided that the pH of the aqueous solution is within the above range.

In addition to the salt of 2-(methoxy-carbonylamino)-benzimidazole, the solutions can also contain other constituents, eg. corrosion inhibitors, wetting agents, dyes or additional fungicidal active ingredients.

The novel fungicides can be used, for example, as preservatives for stored products or against blue stain.

For the purposes of the invention, wood means both wood itself and wood products, eg. wood chips, pulp or intermediates obtained in papermaking from wood. The novel agents are also suitable for protecting industrial materials, for example paper stock, water in cooling plants and paints against fungal attack.

The salts of 2-(methoxy-carbonylamino)-benzimidazole are obtained by intermixing the BCM with an approximately 30–70% strength by weight solution of the corresponding acid in water, with stirring, and stirring the mixture until the BCM has completely dissolved. As a rule, a clear solution is obtained which solidifies, forming crystals, after one or two hours. If the salt does not crystallize out, the salt solution can be used as such.

The salts can be isolated as solids, and are readily soluble in water. They are preferably prepared in the form of aqueous solutions and are used in this form without intermediate isolation of a solid. The salts have, for example, the following composition:
1 mole of BCM. 2 moles of 4-phenolsulfonic acid
1 mole of BCM. 2 moles of sulfamic acid
1 mole of BCM. 2 moles of HBF$_4$.

EXAMPLE 1

1 mole of 2-(methoxy-carbonylamino)-benzimidazole was added to a 60% strength aqueous solution of 2 moles of 4-phenolsulfonic acid, while stirring. The 2-(methoxy-carbonylamino)-benzimidazole dissolved, the solution becoming slightly warm. The clear, slightly viscous solution solidifies after 1 or 2 hours, and the product was able to be dried, comminuted and used for the preparation of aqueous solutions of the salt without further treatment. The dry salt had a melting point of 200° C.

EXAMPLE 2

BCM was introduced into a vacuum kneader of suitable size and was mixed in the dry state with sulfamic acid (NH$_2$SO$_3$H) in a molar ratio of 1:2 for about 15 minutes. 10% by weight of distilled water, based on the mixture, was then added and the paste which formed was kneaded for not less than 30 minutes. The reaction is exothermic, so that cooling may be required, depending on the quantity of the mixture.

Reduced pressure was then applied to the kneader, and the water was removed, while kneading. Depending on the quantity, it may be advantageous to heat the mixture to 40° C. After about 1 hour, the kneader contained the dry reaction mixture in fine-particled form.

The BCM-sulfamic acid salt of melting point 175° C. thus obtained dissolved in water giving a clear solution.

Because of the excellent water-solubility of the salts, distribution of the active ingredient 2-(methoxy-carbonylamino)-benzimidazole on the parts of the plants to be protected is substantially better than when a corresponding active ingredient suspension of varying particle size is used. In addition, the uptake of active ingredient via the roots, leaves and shoots is promoted, and the systemic activity is intensified.

Examples of fungal diseases which can be controlled with the fungicide according to the invention are powdery mildew of vines, apples, Cucurbitaceae and ornamental plants, eg. roses, zinnias and phlox, *Botrytis cinerea* in vines, paprika, strawberries and hops, species of Monilia, *Sclerotinia sclerotiorum* in rapeseed, *Cercosporella herpotrichoides* in wheat, *Septoria nodorum* in wheat, species of Fusarium, *Cercospora kikichii, C. sojinae, Diaporthe phaseolorum,* Phomopsis in soybeans, *Cercospora personata* in groundnuts, *Venturia inaequalis* in apples and pears, *Ceratocystis ulmi* in elms, brown rot of fruit caused by Pencillium species, and species of Ustilago in cereals and cane sugar.

The amounts applied depend on the type of effect desired, and are from 0.05 to 3 kg or more of active ingredient per ha, calculated as 2-(methoxy-carbonylamino)-benzimidazole. Immersion or injection solutions contain, for example, from 0.025 to 1% by weight of active ingredient, calculated as 2-(methoxycarbonylamino)-benzimidazole.

For preserving wood, the agents can be applied, for example,
(a) by spraying the wood with the solution,
(b) by immersing the wood in the solution,
(c) by impregnating the wood in a vessel under pressure, or
(d) by brushing onto the wood.

In the case of wood products, eg. wood chips and pulp, and other industrial products which are susceptible to fungal or bacterial attack, eg. intermediates obtained in papermaking, the agents are applied by suitable industrially feasible methods.

The effectiveness of the fungicides in the field of wood preservation extends to
(a) molds (eg. *Aspergillus niger*),
(b) wood root fungi (eg. *Chaetomium globosum*),
(c) blue stain fungi (eg. *Pullularia pullulans*), and
(d) bacteria, and, in higher concentrations, also to
(e) wood-destructive fungi (eg. *Serpula lacrymans*).

Use in wood preservation shows surprising advantages.
(1) The solution penetrates the wood or wood products well.
(2) As a result of the solution being acid, the wood does not swell, which would prevent penetration of the aqueous solution into the wood.
(3) As a result of the buffer action of the wood, the pH of the solution which has penetrated is increased and the active ingredient is thus released from the acid solution.

The following list of fungicidal active ingredients with which the compounds according to the invention may be combined is intended to illustrate and not to restrict the combination possibilities. Examples are as follows:

sulfur, dithiocarbamates and their derivatives, e.g. iron-(III) dimethyldithiocarbamate, zinc dimethyldithiocarbamate, manganese N,N-ethylene-bis-dithiocarbamate, manganese zinc N,N-ethylenediamine-bis-dithiocarbamate, zinc N,N-ethylene-bis-dithiocarbamate, tetramethylthiuram disulfide, the ammonia complex of zinc N,N-ethylene-bis-dithiocarbamate and N,N'-polyethylene-bis-(thiocarbamoyl)-disulfide, zinc N,N'-propylene-bis-dithiocarbamate, and the ammonia complex of zinc N,N'-propylene-bis-dithiocarbamate and N,N'-polypropylene-bis-(thiocarbamoyl)-di-sulfide; nitro derivatives, e.g. dinitro-(1-methylheptyl)-phenyl crotonate, 2-sec.-butyl-4,6-dinitrophenyl 3,3-dimethylacrylate and 2-sec.-butyl-4,6-dinitrophenyl isopropyl carbonate; heterocyclic compounds, e.g. N-(1,1,2,2-tetrachloroethylthio)tetrahydrophthalimide, N-trichloromethylthiotetrahydrophthalimide, N-trichloromethylthiophthalimide, 2-heptadecyl-2-imidazoline acetate, 2,4-dichloro-6-(o-chloroanilino)-s-triazine, O,O-diethyl phthalimidophosphonothioate, 5-amino-1-(bis-(dimethylamino)-phosphinyl)-3-phenyl-1,2,4-triazole, 5-ethoxy-3-trichloromethyl-1,2,4-thiadiazole, 2,3-dicyano-1,4-dithiaanthraquinone, 2-thio-1,3-dithio-(4,5-b)-quinoxaline, methyl 1-(butylcarbamoyl)-2-benzimidazolecarbamate, 2-methoxycarbonylamino-benzimidazole, 2-thiocyanatomethylthio-benzthiazole, 4-(2-chlorophenylhydrazono)-3-methyl-5-isoxazolone, pyridine-2-thio-1-oxide, 8-hydroxyquinoline and its copper salts, 2,3-dihydro-5-carboxanilido-6-methyl-1,4-oxathiine-4,4-dioxide, 2,3-dihydro-5-carboxanilido-6-methyl-1,4-oxathiine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various compounds, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N', N'-dimethyl-N-phenyl-sulfuric acid diamide, 2,5-dimethylfuran-3-carboxylic acid anilide, 2,5-dimethylfuran-3-carboxylic acid cyclohexylamide, 2-cyano-N-(ethylaminocarbonyl)-2-(methoxyimino)-acetamide, 2-methyl-benzoic acid anilide, 2-iodo-benzoic acid anilide, 1-(3,4-dichloroanilino)-1-formylamino-2,2,2-trichloroethane, 2,6-dimethyl-N-tridecyl-morpholine and its salts, 2,6-dimethyl-N-cyclododecyl-morpholine and its salts, DL-methyl-N-(2,6-dimethylphenyl)-N-fur-2-oyl-alanate, methyl DL-N-(2,6-dimethylphenyl)-N-(2'-methoxyacetyl)-alanate, diisopropyl 5-nitroisophthalate, 1-(1', 2', 4'-triazol-1'yl)-1-(4-chloro-phenoxy)-3,3-dimethylbutan-2-one, 1-(1', 2', 4'-triazol-1'-yl)-1-(4'-chlorophenoxy)-3,3-dimethylbutan-1-ol, N-(2,6-dimethylphenyl)-N-chloroacetyl-D,L,2-aminobutyrolactone, and N-(n-propyl)-N-(2,4,6-trichlorophenoxyethyl)-N'-imidazolylurea.

EXAMPLE 3

Action on *Botrytis cinerea* in pimientos

Pimiento seedlings of the "Neusiedler Ideal Elite" variety were sprayed, after 4 to 5 leaves were well developed, to runoff with aqueous suspensions of a salt according to Example 1 containing 0.025, 0.05 and 0.1% of active ingredient, calculated as 2-(methoxycarbonylamino)-benzimidazole. After the sprayed-on layer had dried, the plants were sprinkled with a conidial suspension of the fungus *Botrytis cinerea*, and placed at 22° C. to 24° C. in a chamber of high humidity. After 5 days, the disease had spread to such a great extent on the untreated plants that the necroses covered the major portion of the leaves. The fungicidal action was assessed as follows: 0=no fungus attack, graduated down to 5=total attack. Leaf attack further spraying with solution containing active ingredient in amounts of

| Active ingredient | 0.1% | 0.05% | 0.025% | 0.012% | 0.006% | 0.003% |
|---|---|---|---|---|---|---|
| Ex. 1 BCM salt of 4-phenolsulfonic acid | 0 | 0 | 1 | 1 | 2 | 2 |
| Ex. 2 BCM salt of sulfamic acid | 0 | 0 | 0 | 0 | 0 | 1 |
| BCM (prior art) | 0 | 1 | 1 | 2 | 3 | 3–4 |
| Control (untreated) | | | 4–5 | | | |

EXAMPLE 4

The action of the active ingredient described in Example 1 on the wood-discoloring fungi *Schlerophoma pityophila* and *Pullularia pullulans* was assessed. Pine sapwood boards were coated, in 2 separate operations, with $2 \times 100$ g/m² of wood surface area of aqueous solutions containing 0.25, 0.5 and 1% of active ingredient, based on BCM. The control surfaces were coated with the same amounts of linseed oil varnish. After a colorless alkyd resin paint had been applied, the boards were weathered for 6 months in the open. To test the action of the compounds on the fungi, the boards were then placed in glass dishes containing the fungi. Upon completion of the test, 90% (on average) of the control surfaces had been stained blue as a result of the growth of *Schlerophoma pityophila* and *Pullularia pullulans*. The results are given below.

| Active ingredient amount in g/m² in wood surface area | Blue stain | Stain-free zone in mm (depth of action) |
| --- | --- | --- |
| 0.5 | 0 | more than 3 |
| 1.0 | 0 | more than 3 |
| 2.0 | 0 | more than 3 |
| Control (no active ingredient) | 3 | 0 |

0 = no sign of fungus attack
1-3 = stages up to total fungus attack

The following examples illustrate the composition of wood perservatives.

EXAMPLE 5

0.40% (wt. %) BCM
0.80% 4-phenolsulfonic acid
0.20% control dye (tartrazine yellow)
0.20% corrosion inhibitor (benzotriazole)
98.40% water.

EXAMPLE 6

0.40% BCM
0.80% 4-phenolsulfonic acid
0.20% corrosion inhibitor (benzotriazole)
98.60% water.

EXAMPLE 7

0.40% BCM
0.30% fluoboric acid ($HBF_4$)
1.00% wetting agent (p-nonylphenol ethoxylate (EO=7-12))
0.50% dye (tartrazine yellow)
97.80% water.

We claim:
1. A salt of 2-(methoxy-carbonylamino)-benzimidazole with 4-phenolsulfonic acid or with sulfamic acid.
2. The salt of claim 1 with 4-phenolsulfonic acid.

* * * * *